(12) United States Patent
Katiyar

(10) Patent No.: US 10,160,709 B2
(45) Date of Patent: Dec. 25, 2018

(54) GLYCOL ETHER PROCESS

(71) Applicant: Scientific Design Company, Inc., Little Ferry, NJ (US)

(72) Inventor: Saurabh Katiyar, Little Ferry, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 15/672,927

(22) Filed: Aug. 9, 2017

(65) Prior Publication Data

US 2018/0044272 A1    Feb. 15, 2018

Related U.S. Application Data

(60) Provisional application No. 62/372,649, filed on Aug. 9, 2016.

(51) Int. Cl.
| | | |
|---|---|---|
| C07C 41/42 | (2006.01) |
| B01D 5/00 | (2006.01) |
| C07C 43/13 | (2006.01) |
| B01D 3/06 | (2006.01) |
| B01D 3/14 | (2006.01) |
| B01D 19/00 | (2006.01) |

(52) U.S. Cl.
CPC ............... *C07C 41/42* (2013.01); *B01D 3/06* (2013.01); *B01D 3/148* (2013.01); *B01D 5/009* (2013.01); *B01D 19/0015* (2013.01); *C07C 43/13* (2013.01)

(58) Field of Classification Search
CPC .......... C07C 41/42; C07C 41/40; B01D 5/009
See application file for complete search history.

(56) References Cited

U.S. PATENT DOCUMENTS

| | | |
|---|---|---|
| 3,563,914 A | 2/1971 | Wattimena |
| 3,702,259 A | 11/1972 | Nielsen |
| 3,935,279 A | 1/1976 | Cocuzza et al. |
| 4,761,394 A | 8/1988 | Lauritzen |
| 4,766,105 A | 8/1988 | Lauritzen |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,187,140 A | 2/1993 | Thorsteinson et al. |
| 5,407,888 A | 4/1995 | Herzog et al. |
| 6,264,800 B1 | 7/2001 | Gupta |
| 6,372,925 B1 | 4/2002 | Evans et al. |
| 2007/0037991 A1 | 2/2007 | Rizkalla |

FOREIGN PATENT DOCUMENTS

| | | |
|---|---|---|
| CN | 103694088 A | 4/2014 |
| JP | 2013209329 A | 10/2013 |

OTHER PUBLICATIONS

International Search Report dated Nov. 17, 2017 with Written Opinion received in a corresponding foreign application.

*Primary Examiner* — Rosalynd A Keys

(74) *Attorney, Agent, or Firm* — Scully Scott Murphy and Presser

(57) ABSTRACT

A process for the preparation of glycol ethers by providing a diethylene glycol ether column bottoms mixture comprising triethylene glycol ether, tetraethylene glycol ether, and glycol ether catalyst; separating, in a stripping column, the column bottom mixture into a triethylene glycol ether vapor overhead and a liquid bottoms; and separating, in an evaporator, the liquid bottoms into a residue containing about 80% to about 90% tetraethylene glycol ether and an evaporator overhead comprising at least about 60% tetraethylene glycol ether.

11 Claims, 3 Drawing Sheets

GLYCOL ETHER PROCESS

CROSS REFERENCE TO RELATED APPLICATION

The present invention claims the benefit of U.S. Provisional Patent Application No. 62/372,649 filed Aug. 9, 2016, the entire content and disclosure of which is incorporated herein by reference.

FIELD OF THE INVENTION

The present invention relates to a method for improving overall yield of glycol ether process by better recovery of tetraethylene glycol ethers.

BACKGROUND OF THE INVENTION

Glycol ethers, the products of reaction between ethylene oxide and an alcohol have been a well-known industrial chemical since the 1930s, but it is only since the 1970s that they began to be extensively used. Glycol ethers are hydrocarbons with both alcohol and ether functional groups, making them a highly versatile and widely-used class of industrial chemicals with a wide range of applications in many different product areas. Because they are polar molecules and possess the strong hydrogen bonding characteristics of the alcohol and ether functional groups, glycol ethers are miscible in water and in organic solvents. This dual functionality gives glycol ethers the unique ability to solubilize many types of chemicals, so glycol ethers are commonly used as solvents in industrial processes and manufacturing as well as thinner and rheology modifiers in water-based paints, coatings and cleaning solutions. Glycol ethers that comprise longer chain alcohols are miscible in and can solubilize nonpolar organic compounds and oils and so can serve in many other industrial applications such as colorants, plasticizers, and lubricants.

Historically, methanol was most often selected for reaction with ethylene oxide and the resulting mono- and diethylene glycol methyl ethers occupied the largest segment of the glycol ether market. However, in recent years, ethylene glycol butyl ether, made from the reaction of butanol and ethylene oxide, and its higher molecular weight homologues have become of particular interest for their use as solvents, industrial chemicals and chemical intermediates. In fact, production of this butyl family of glycol ethers has risen much faster than many other families of glycol ethers since the 1970s, displacing other solvent products for both environmental and health reasons. (See P. de Ketttenis, Historic and Current use of glycol ethers: a picture of change, *Toxicology Letters*, 156, 5-11 (2005). doi:10.1016j.toxlet.2003.12.076).

In view of the increasing importance of these glycol ether chemical families it has become necessary to ensure continued process development and refinement to maximize process economics and efficiency. For example, historically it was taught that glycol ether manufacturing processes should be designed and operated to maximize the making of mono- and diethylene glycol ether and not higher molecular weight products. Thus, U.S. Pat. No. 3,935,279 teaches that while mono- and diethylene glycol ether had economic value and their production should be maximized, higher molecular weight homologues such as tri- and tetraethylene glycol ether were essentially waste products to be disposed of.

However, as glycol ether products increase in importance, it has become less and less desirable to simply dispose of a significant amount of manufactured product especially as these higher molecular weight homologues such as tri- and tetra-ethylene glycol ether have value and are particularly useful in high boiling point applications. Thus, improvements to the process to enhance higher molecular weight glycol ether recovery would not only increase the recovery of heavy products but also improve the overall yield of the process itself.

Accordingly, there is a continuing need in the art for a glycol ether process, in which a suitable amount of higher molecular weight homologues, especially tetraethylene glycol ethers, are recovered during the process.

BRIEF SUMMARY OF THE INVENTION

The present invention relates to a process for the preparation of glycol ethers comprising the steps of: (a) providing a diethylene glycol ether column bottoms mixture comprising triethylene glycol ether, tetraethylene glycol ether, and a glycol ether catalyst; (b) separating, in a stripping column, into a pure triethylene glycol ether liquid overhead and a liquid bottoms; and (c) separating, in an evaporator, the liquid bottoms into a residue containing about 80% to about 90% tetraethylene glycol ether along with spent catalyst and an evaporator overhead comprising at least about 60% tetraethylene glycol ether.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
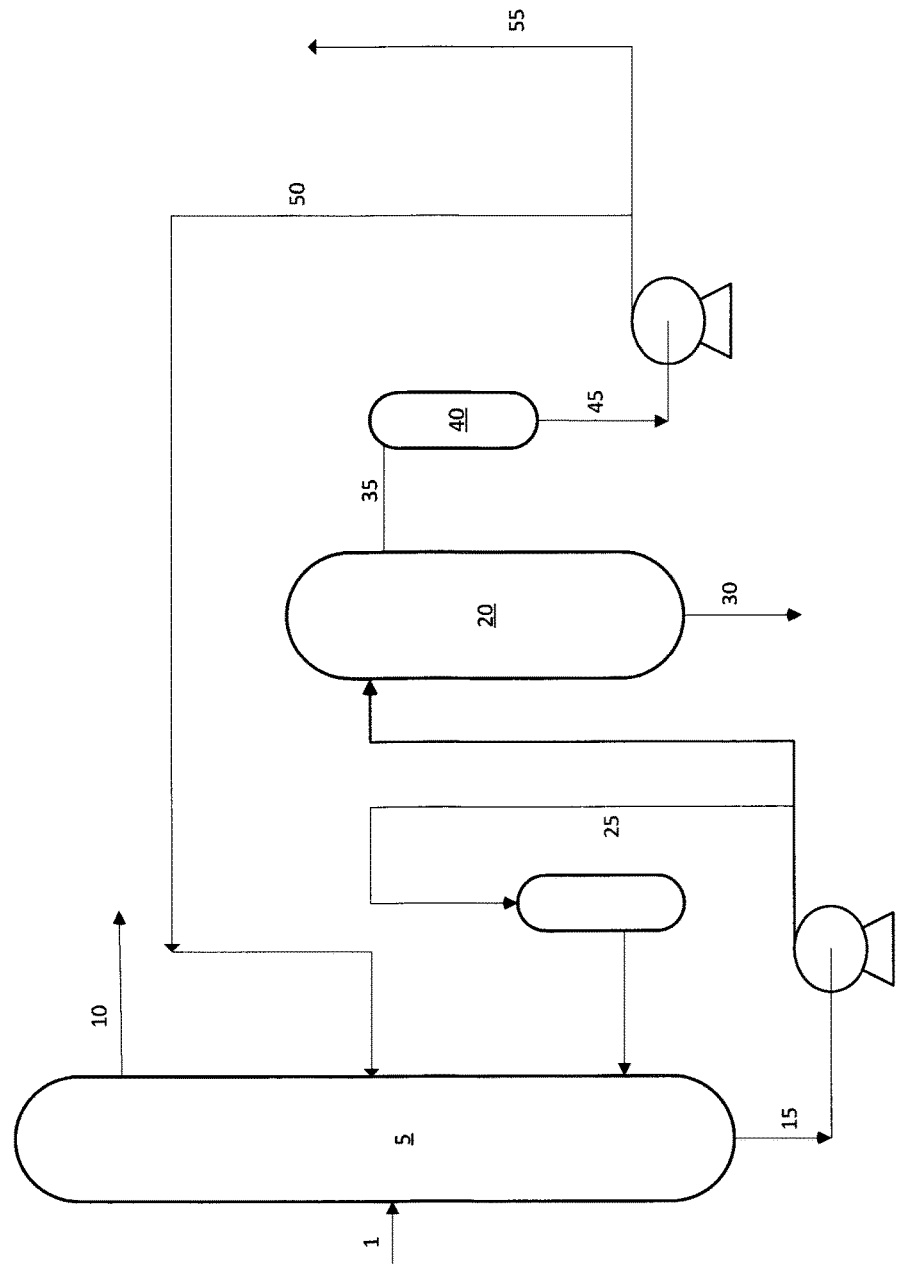
FIGS. 1-3 are schematic flow sheets for process embodiments for preparing glycol ethers according to the present invention.

All parts, percentages and ratios used herein are expressed for ethylene glycol butyl ether by weight unless otherwise specified. All pressures are absolute. All documents cited herein are incorporated by reference.

Glycol ethers are commercially manufactured by the catalyzed reaction of ethylene oxide with an alcohol. Ethylene oxide may also react directly with monoethylene glycol ether and higher homologues to form diethylene, triethylene and tetrathylene glycol ether and higher homologues. Although there is no theoretical limit to the size of the molecule chain that can be made, tetraethylene glycol ether, which is the primary focus of the present patent application, is usually the highest homologue obtained.

The reaction of ethylene oxide and alcohol to form ethylene glycol monoether and higher molecular weight homologues is controlled by a number of parameters, the first of which is the use of a catalyst. The catalyst is typically a homogeneous base catalyst such as an alkali metal alkoxide, preferably alkali metal hydroxide, more preferably potassium hydroxide. While the catalyst has a beneficial effect on the kinetics and selectivity of the reaction, it presents a problem that the catalyst has to be separated from the higher molecular weight reaction products. The catalyst is separated from monoethylene and diethylene glycol ethers in separation columns (discussed below) as the product is taken overhead while the catalyst leaves the column in the column bottoms. However, such separation becomes more difficult with higher molecular weight products. As a result, in glycol ether processes of the prior art typically the heavier reaction products and especially tetraethylenc glycol ethers were not recovered. By the present invention a process has been developed that allows for the recovery of tetraethylene glycol ethers.

A second parameter that affects the reaction of ethylene oxide and alcohols is the molar ratio of ethylene oxide to alcohol—as this ratio increases, more diethylene glycol ether and higher homologs will be produced: the typical concentration will be diethylene glycol ether 18% to 22%, triethylene glycol ether 4% to 9%, and tetraethylene glycol ether 0.5% to 1.5%. Similarly, recycling of monoglycol ethers back to the reactor decreases the amount of monoethylene glycol ethers while increasing the amount of diethylene glycol ethers and other higher homologs.

Any suitable alcohol can be chosen for the initial reaction with ethylene oxide; particularly preferred are methanol, ethanol, and butanol.

In a conventional process for the manufacture of glycol ethers (not shown), the glycol ether is produced in the anhydrous liquid phase by reacting ethylene oxide with an alcohol in one or more glycol ether reactors. In the presence of excesses alcohol, nearly all of the ethylene oxide is reacted and as mentioned above, depending on the ratio of alcohol to ethylene oxide and the presence of a recycle of monoglycol ethers back into the reactor will result in a specific product mixture of mono-, di-, tri-, and, tetra-ethylene glycol ether. Reactor effluent is then passed from the glycol ether reactor to the alcohol recycle column, where alcohol is distilled overhead and recycled to the glycol ether reactor. The bottoms from the alcohol recycle column, comprising the product mixture of glycol ethers described above as well as catalyst and other heavies, is then sent to the monoethylene glycol ether column where monoethylene glycol ether is distilled and the high purity monoethylene glycol ether is drawn as a side stream liquid and sent to storage; while the bottom's product from the monoethylene glycol ether column, comprising diethylene glycol ether, heavier glycol ethers, and catalyst is sent to the diethylene glycol ether column. In the diethylene glycol ether column, where diethylene glycol ether is distilled and the high purity diethylene glycol ether is drawn as a side stream and sent to product storage. The process is again repeated with the bottoms from the diethylene glycol ether column, which are sent to a triethylene glycol ether column.

FIG. 1 shows a triethylene glycol ether stripping column 5, which is maintained under relative vacuum pressures of about 10 mm Hg to about 25 mm Hg. The temperature at the bottom of the column is between about 185° C. to about 195° C. The triethylene glycol ether column preferably contains packing for its internals. The aforementioned bottoms from the diethylene glycol ether column are provided as stream 1 to the triethylene glycol ether column 5. The purified triethylene glycol ether is distilled out and sent as a rich triethylene glycol ether liquid side stream 10 to product storage (not shown).

In prior art processes, the liquid bottoms from the triethylene glycol ether column, comprising mostly tetraethylene glycol ether and triethylene glycol ether would then be purged and used as fuel or sewered. This is because until the present invention it has been difficult to recover the tetraethylene glycol ether. But using such material for fuel or otherwise disposing it represents a loss of material with an economic value. By the present invention, process schemes have been developed which allow for the recovery of this valuable material.

Thus, in the present invention, this liquid bottoms stream 15, which comprises approximately 40 to 60% tetraethylene glycol ether and 40% to 60% triethylene glycol ether, is sent to an evaporator 20, with a portion of the bottoms stream 15 diverted as a reboiler side stream 25 to the adjacent reboiler to provide boil-up duty. Preferably the evaporator 20 is a wiped film evaporator in which a drive motor turns a rotor inside the cylindrical evaporator housing in which is disposed a heat jacket. The liquid bottoms stream that is fed to the evaporator gradually spirals down the inner diameter evaporator wiped film evaporator housing being in constant thermal contact with the heating medium in the heat jacket. A wiped film evaporator is preferred for this application because the evaporator is maintained at a low pressure of between about 3 mm Hg and about 5 mm Hg, and because the content of the of the evaporator is relatively viscous due to the presence of not only tetraethylene glycol ether but additional viscosity-imparting components such as spent catalyst.

The evaporator 20 is maintained at a high temperature and (along with the adjacent condenser) low pressure in order to maximize the distillation of tetraetheylene glycol ether out of the tetraetheylene glycol ether bottoms stream 15 supplied to the evaporator to create an evaporator overhead 35, which contains at least about 60% tetraetheylene glycol ether, with the balance comprising triethylene glycol ether and heavier glycol ether homologs. Preferably in the evaporator the temperature is maintained between about 160° C. to about 170° C. The resulting bottoms residue stream 30 comprises between about 80% and about 90% tetraethylene glycol ether, 5% to 15% triethylene glycol ether along with spent catalyst and heavier glycol ether homologs. Normally this bottoms products, the glycol ether component of which could constitute as much as 0.25 to 1.75 wt % of total production, would be disposed of or burnt for fuel or heat, but by the present invention this retained glycol ether product can be recovered and sold as product.

The evaporator overhead 35 flows from the evaporator to the condenser 40 by a small pressure differential; the evaporator and the condenser are preferably operated in communication as part of the same ejector system in order to maintain a low pressure across both units with the ejector system drawing a vacuum from the evaporator across the condenser. The resulting condensed stream 45 is divided into a recycle stream 50 and a product steam 55. The recycle steam 50 is sent back to the triethylene glycol ether column 5 as reflux. The product stream 55 is withdrawn from the process and sent to tetraethylene glycol product storage. This product steam 55 is identical in composition to the evaporator overhead 35. Again, like the residue stream 30 recovered from bottoms of the evaporator 20, this recovered tetraethylene glycol ether even if it is of relatively low purity nonetheless represents a product with a monetary value that before this invention was simply burned for fuel or disposed of.

The ratio of the recycle stream 50 that is sent back to the triethylene glycol ether column 5 compared to the amount that is taken as product stream 55 and removed from the process loop is regulated by a temperature controller (not shown) to ensure that the operating temperature of the triethylene glycol ether column 5 is maintained within the aforementioned temperature range. As the volume ratio of product stream 55 to recycle stream 50 increases, the temperature in the triethylene glycol ether column 5 will tend to increase; accordingly, the temperature controller will act to maintain the relative flow of product stream 55 to recycle stream 50 to keep the triethylene glycol ether column 5 within the temperature range of about 185° C. to about 195° C.

Figure 2:
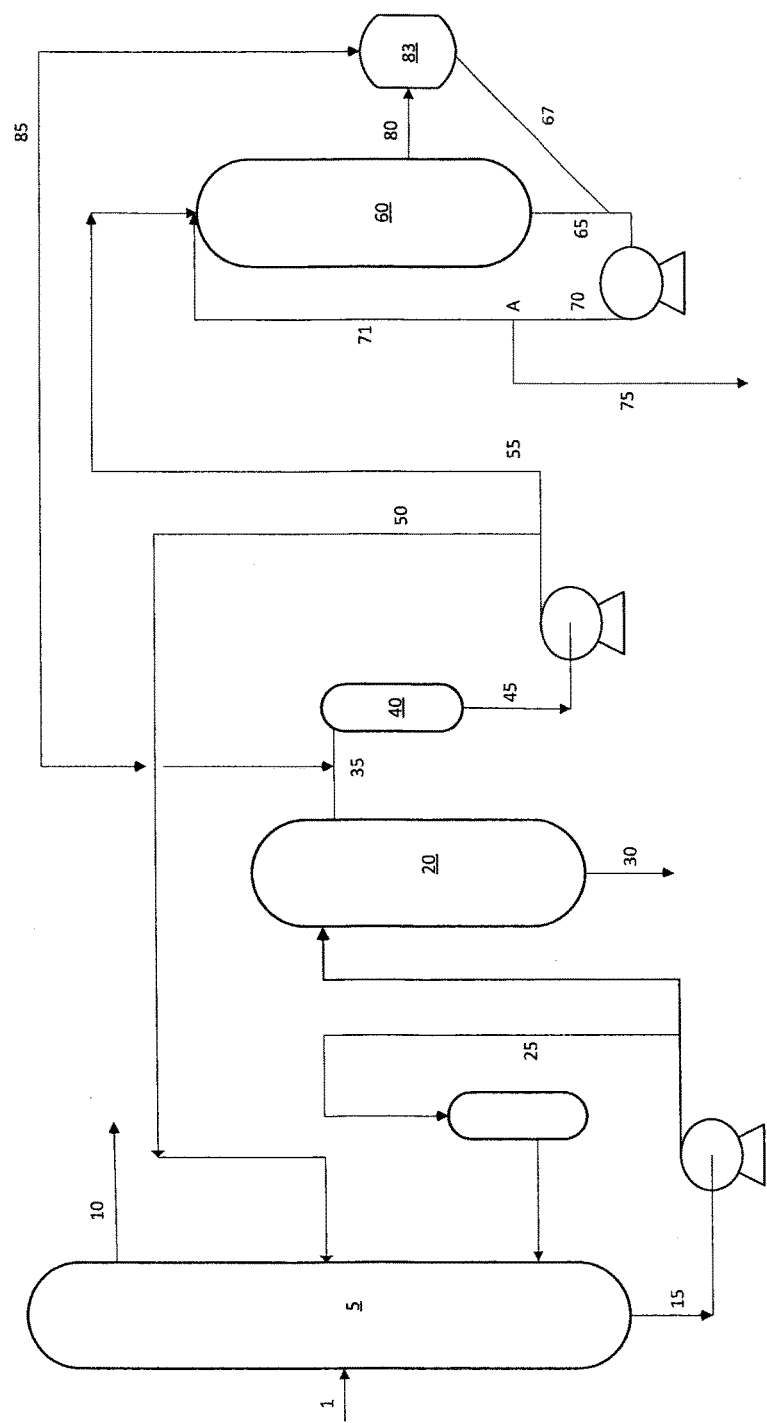

In a second embodiment, the above process is modified somewhat as shown in FIG. 2. This second embodiment allows for the production of tetraethylene glycol ether of increased purity compared to that produced in embodiment 1. The second embodiment functions similar to the first embodiment (operated within identical temperature and pressure ranges) except that product stream 55 is not immediately recovered but instead is sent to a second evaporator 60 in series communication with the evaporator 20. Like in the first embodiment, in this embodiment the stream 45 is divided into a product steam 55 and recycle stream 50 to keep the triethylene glycol column 5 within the aforementioned temperature of about 185° C. to about 195° C.

The second evaporator 60 is preferably a falling film evaporator. The second evaporator 60 is preferably operated at a temperature between about 160° C. to about 170° C. and a pressure of between about 2 mm Hg and about 3 mm Hg. In the second evaporator 60 a product bottoms solution is formed in the bottoms of the second evaporator. This product solution is taken as a liquid bottoms stream 65 and then combined with the drum condensate stream 67 from the evaporator drum 83 to form a condensate-product solution stream 70, which is then pumped to junction A. The condensate-product solution stream comprises from about 70% to about 80% tetraethylene glycol ether. At junction A, the condensate-product solution stream 70 is divided and a portion of the condensate-product solution stream is returned as reflux 71 to the second evaporator 60 and another portion is withdrawn through pipe 75 from the process as medium purity tetraethylene glycol ether product solution. This product solution has identical composition to the aforementioned condensate-product solution stream. Again, before the present invention this valuable product with substantial economic value would have simply been disposed of.

The more volatile components in the second evaporator 60 are separated as a vapor phase from the liquid bottoms components and sent as the second evaporator vapor sidestream 80 to the evaporator drum 83. In the evaporator drum, a condensate of heavier components is formed in the bottom of the evaporator drum. A level controller (not shown) on the evaporator drum regulates the level of the condensate in the bottom of the evaporator drum 83, with the level controller regulating the flow of the medium purity tetraethylene glycol ether product solution 75. The evaporator drum vapor overhead stream 85 flows back to the condenser 40.

Figure 3:
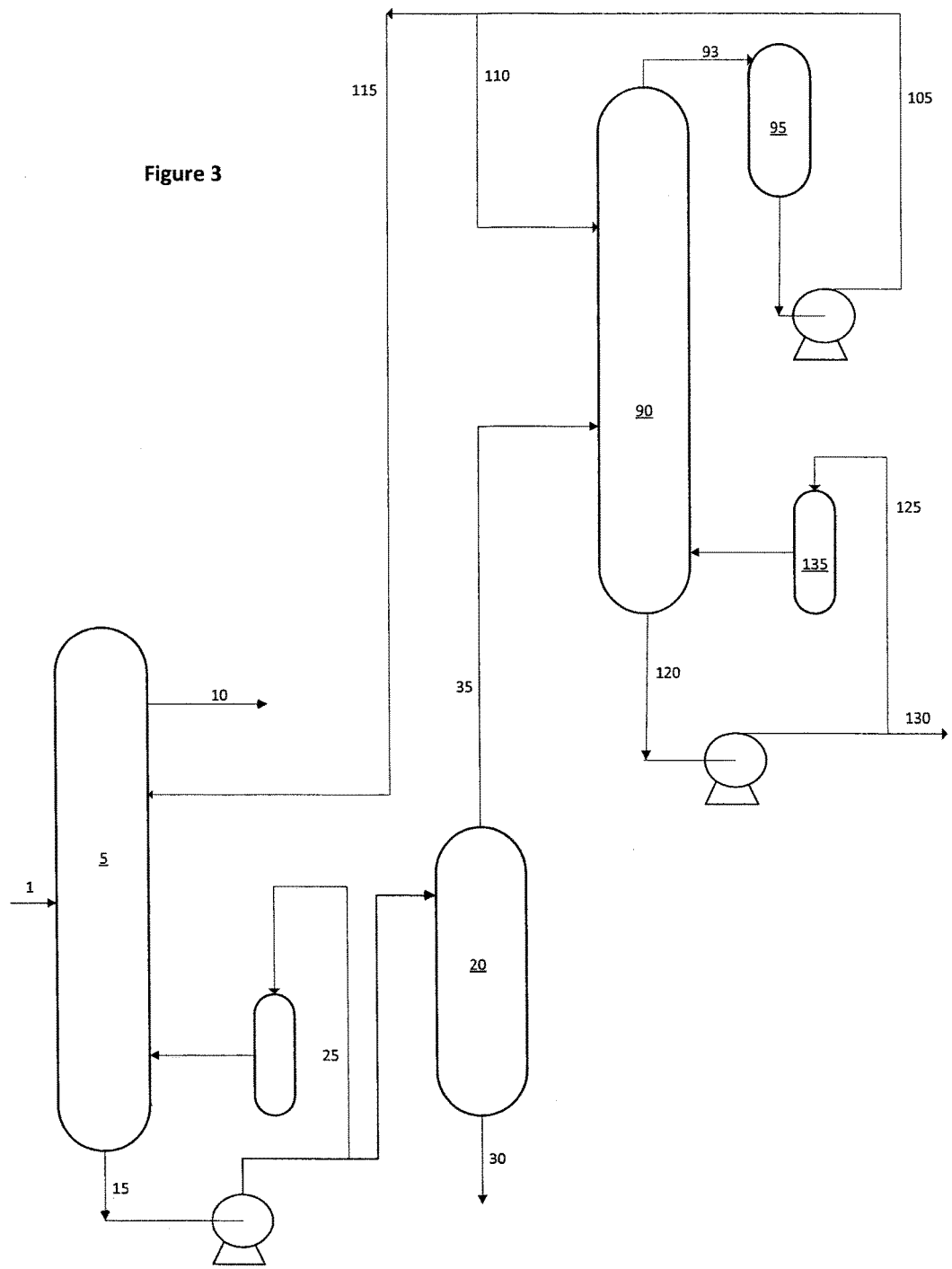

In a third embodiment, the first embodiment is modified as shown in FIG. 3. This third embodiment allows for the production of high purity tetraethylene glycol ether. This third embodiment functions similarly to the first embodiment (operated within identical temperature and pressure ranges) except the evaporator overhead 35 is not immediately recovered but instead is sent to a second stripping shown in FIG. 3 as the tetraethylene glycol ether stripping column 90. The tetraethylene glycol ether column 90 is operated at a pressure of about 2 mm Hg to about 5 mm Hg and a temperature between about 150° C. to about 160° C. The column bottoms are taken as tetraethylene glycol ether stripping column bottoms stream 120, which contains at least about 90% tetraethylene glycol ether. Stream 120 is then divided into a return stream 125 sent to the reboiler 135 and a high purity product stream 130. This high purity product stream has the same composition as the tetraethylene glycol ether stripping column bottoms stream 120. This is again, material that until the present invention would not have been recovered.

The overhead vapor from the tetraethylene glycol ether stripping column 90 flows by a small pressure differential through conduit 93 to condenser 95 which is preferably maintained under a near vacuum pressure of from about 2 mm Hg to about 3 mm Hg. Preferably, the tetraethylene glycol ether column and the condenser are operated in communication as part of the same ejector system in order to maintain a low pressure across both units with the ejector system drawing a near vacuum from the tetraethylene glycol ether column across the condenser. The condensate is then pumped as stream 105 where it is divided into a first portion 110 that is sent as a reflux stream to the tetraethylene glycol ether column 90 and a second portion 115 that is returned as reflux to the triethylene glycol ether column 5.

The triethylene glycol ether column 5, tetraethylene glycol ether column 90, and the first evaporator 20 and second evaporator 60 are constructed so as to facilitate intimate vapor-liquid contact and in addition to the preferred devices specified for 20 and 60, above, any suitable arrangement or configuration that accomplishes this is acceptable. The columns' internals may be selected from a structured packing arrangement.

Ethylene Oxide Production

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 43% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process. Both have adverse effects on the catalyst, so the concentrations of these components are usually kept at a minimum.

Also present in the reaction, as previously mentioned, are one or more chloride moderators. Non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

A usual method for the ethylene epoxidation process comprises the vapor-phase oxidation of ethylene with molecular oxygen, in the presence of an epoxidation catalyst (to be defined in greater detail herein below), in a fixed-bed tubular reactor. Conventional, commercial fixed-bed ethylene-oxide reactors are typically in the form of a plurality of parallel elongated tubes (in a suitable shell) approximately 20 to 70 mm O.D. and 15 to 65 mm I.D. and 5-16 meters long filled with catalyst. Such reactors include a reactor outlet which allows the olefin oxide, un-used reactants, and byproducts to exit the reactor chamber.

The ethylene oxide that is reacted with an alcohol in the present invention may be supplied from OSBL or may be supplied by an ethylene oxide process that is integrated with the glycol ethers process in the same chemical complex.

Epoxidation Catalyst

The epoxidation catalyst that can be used in the present invention includes a silver-based epoxidation catalyst that has a selectivity of greater than 83 mole %. The silver-based epoxidation catalyst that can be used in the present invention includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. In one embodiment of the present application, the epoxidation catalyst that can be used is a silver-based, rhenium-containing epoxidation catalyst which may also include one or more additional promoters. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. Equivalent diameter is the diameter of a sphere having the same external surface (i.e., neglecting surface within the pores of the particle) to volume ratio as the support particles being employed.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

In some embodiments of the present invention, a promoting amount of a rhenium component, which may be a rhenium-containing compound or a rhenium-containing complex is also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and, if present, rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), optional rhenium component, and optional additional promoter(s) will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include operability (resistance to runaway), selectivity, activity, conversion, stability and yield, among other catalytic properties. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoters can be employed.

After impregnation of the support with the silver-containing compound, i.e., a silver precursor, optional promoters such as, for example, rhenium and/or alkali metals, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 h$^{-1}$, a reactor inlet pressure of 1 MPa to 3 MPa, a coolant temperature of 180-315° C., an oxygen conversion level of 10-60%, and an EU production rate (work rate) of 100-350 kg EO/m$^3$ catalyst/hr and a change in ethylene oxide concentration, $\Delta$EO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

I claim:

1. A process for the preparation of glycol ethers comprising the steps of:
    (a) providing a diethylene glycol ether column bottoms mixture comprising triethylene glycol ether, tetraethylene glycol ether, and a glycol ether catalyst;
    (b) separating, in a stripping column, the diethylene glycol ether column bottoms mixture into a triethylene glycol ether vapor overhead and a liquid bottoms; and
    (c) separating, in a first evaporator, the liquid bottoms into a residue stream containing about 80 weight % to about 90 weight % tetraethylene glycol ether and an evaporator overhead comprising at least about 60 weight % tetraethylene glycol ether.

2. The process according to claim 1, further comprising the following steps subsequent to step (c):
    (d) condensing the evaporator overhead to form a condensed stream;
    (e) dividing the condensed stream into a recycle stream and a product stream;
    (f) separating, in a second evaporator, the product stream into a second evaporator vapor sidestream and a second evaporator liquid bottoms; and
    (g) forming a condensate-product solution stream by mixing the second evaporator liquid bottoms with a drum condensate stream, wherein the condensate-product solution stream comprises from about 70 weight % to about 80 weight % tetraethylene glycol ether.

3. The process according to claim 1, further comprising the following steps subsequent to step (c):
    (d1) separating, in a second stripping column, the evaporator overhead into a vapor overhead and a stripping column bottoms stream, wherein the stripping column bottoms stream contains at least about 90 weight % tetraethylene glycol ether.

4. The process according to claim 1, wherein the temperature of the evaporator is maintained between about 160° C. to about 170° C. and the pressure between about 3 mm Hg to about 5 mm Hg.

5. The process according to claim 1, wherein the residue stream comprises approximately 80 weight % to 90 weight % tetraethylene glycol ether and 5 weight % to 15 weight % triethylene glycol ether.

6. The process according to claim 1, wherein the first evaporator is a wiped film evaporator.

7. The process according to claim 2, wherein the second evaporator is a falling film evaporator.

8. The process according to claim 2, wherein the second evaporator is operated at a pressure of about 2 mm Hg to about 3 mm Hg and a temperature between about 110° C. to about 170° C.

9. The process according to claim 2, further comprising the step of passing the evaporator overhead from the first evaporator to provide the second evaporator with a source of vapor and heat.

10. The process according to claim 1, wherein prior to step (a) the process further comprises the step of manufacturing ethylene oxide by contacting an oxygen-containing gas with ethylene in the presence of an epoxidation catalyst.

11. The process according to claim 10, wherein the epoxidation catalyst is a silver-based epoxidation catalyst that includes a promoting amount of rhenium.

* * * * *